US008188026B2

(12) United States Patent
Panandiker et al.

(10) Patent No.: US 8,188,026 B2
(45) **Date of Patent: *May 29, 2012**

(54) LIQUID TREATMENT COMPOSITION

(75) Inventors: Rajan Keshav Panandiker, West Chester, OH (US); Kerry Andrew Vetter, Cincinnati, OH (US); David Scott Dunlop, Mason, OH (US); David Gladney, Jr., Cincinnati, OH (US); Stephen Joseph Hodson, Mason, OH (US); Karl Ghislain Braeckman, Gerpinnes (BE); Karel Jozef Maria Depoot, Anzegem-Vichte (BE); Gayle Marie Frankenbach, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/235,079

(22) Filed: Sep. 22, 2008

(65) Prior Publication Data

US 2009/0069206 A1 Mar. 12, 2009

Related U.S. Application Data

(63) Continuation of application No. PCT/US2007/006984, filed on Mar. 20, 2007.

(60) Provisional application No. 60/815,781, filed on Jun. 22, 2006, provisional application No. 60/784,826, filed on Mar. 22, 2006.

(51) Int. Cl.

| | |
|---|---|
| ***C11D 3/37*** | (2006.01) |
| ***C11D 17/00*** | (2006.01) |
| ***C11D 17/08*** | (2006.01) |
| ***C11D 3/00*** | (2006.01) |
| ***D06M 11/56*** | (2006.01) |
| ***A01H 5/02*** | (2006.01) |

(52) U.S. Cl. ........ 510/276; 510/337; 510/405; 510/416; 510/527; 8/133; 8/137; 8/147

(58) Field of Classification Search .................. 510/276, 510/133, 405, 416, 527; 8/133, 137, 147
See application file for complete search history.

(56) References Cited

U.S. PATENT DOCUMENTS

| | | | |
|---|---|---|---|
| 3,532,635 A | 10/1970 | Hans | |
| 4,145,184 A | 3/1979 | Brain et al. | |
| 4,486,334 A | 12/1984 | Horiuchi et al. | |
| 4,534,892 A | 8/1985 | Suzuki et al. | |
| 4,544,498 A | 10/1985 | Suzuki | |
| 4,717,501 A | 1/1988 | Hirota et al. | |
| 5,017,305 A | 5/1991 | Hoeffkes et al. | |
| 5,089,148 A | 2/1992 | Van Blarcom et al. | |
| 5,308,526 A * | 5/1994 | Dias et al. | 510/159 |
| 5,403,508 A | 4/1995 | Reng et al. | |
| 5,593,614 A | 1/1997 | Laitem et al. | |
| 5,780,411 A | 7/1998 | Erilli | |
| 6,210,659 B1 | 4/2001 | Wilhelm et al. | |
| 6,277,360 B1 * | 8/2001 | Carew et al. | 424/70.12 |
| 6,683,037 B2 | 1/2004 | Mondin et al. | |
| 6,835,700 B1 | 12/2004 | Nieendick et al. | |
| 6,897,253 B2 * | 5/2005 | Schmucker-Castner et al. | 524/291 |
| 6,906,015 B1 * | 6/2005 | Shiloach et al. | 510/130 |
| 6,908,890 B2 | 6/2005 | Oldenhove | |
| 6,943,143 B2 | 9/2005 | Kinloch et al. | |
| 6,956,017 B1 | 10/2005 | Catalan et al. | |
| 2003/0017955 A1 | 1/2003 | Forth et al. | |
| 2003/0199403 A1 * | 10/2003 | Wells et al. | 510/119 |
| 2004/0002438 A1 | 1/2004 | Hawkins et al. | |
| 2004/0092425 A1 | 5/2004 | Boutique et al. | |
| 2004/0121930 A1 | 6/2004 | Wang et al. | |
| 2004/0214740 A1 | 10/2004 | Barberan et al. | |
| 2004/0235690 A1 * | 11/2004 | Oldenhove | 510/130 |
| 2005/0022312 A1 | 2/2005 | Bigorra Llosas et al. | |
| 2005/0048014 A1 | 3/2005 | Linz et al. | |
| 2005/0119151 A1 | 6/2005 | Mayer et al. | |
| 2005/0158268 A1 | 7/2005 | Schmucker-Castner et al. | |
| 2005/0256020 A1 * | 11/2005 | Gardner et al. | 510/392 |
| 2005/0288206 A1 | 12/2005 | Sadlowski et al. | |
| 2006/0005271 A1 | 1/2006 | Turner et al. | |
| 2006/0019866 A1 | 1/2006 | Briggs et al. | |
| 2006/0258558 A1 | 11/2006 | Wachter et al. | |

FOREIGN PATENT DOCUMENTS

| | | |
|---|---|---|
| EP | 0 463 780 A2 | 1/1992 |
| EP | 0 520 551 A2 | 12/1992 |
| EP | 0 535 693 A1 | 4/1993 |
| EP | 1 282 678 B1 | 2/2003 |
| EP | 1 595 939 A1 | 11/2005 |
| JP | 2001-064692 A | 3/2001 |
| JP | 2006-225369 A | 8/2006 |
| WO | WO 98/16538 | 4/1998 |
| WO | WO 99/09944 | 3/1999 |
| WO | WO 01/32715 | 5/2001 |
| WO | WO 01/76552 A2 | 10/2001 |
| WO | WO 02/40627 A2 | 5/2002 |
| WO | WO 2004/014321 | 2/2004 |
| WO | WO 2005/094780 | 10/2005 |
| WO | WO 2006/004876 | 1/2006 |

OTHER PUBLICATIONS

International Search Report mailed Aug. 30, 2007—5 pages.

(Continued)

*Primary Examiner* — Milton I Cano
*Assistant Examiner* — Thuy-Ai Nguyen
(74) *Attorney, Agent, or Firm* — Julie A. McConihay; Steven W. Miller

(57) ABSTRACT

According to the present invention there is provided a pearlescent liquid treatment composition suitable for use as a laundry or hard surface cleaning composition comprising a rheology modifier providing a pouring viscosity at 20 $sec^{-1}$ of from 50 to 700 cps, a viscosity at constant low stress of 0.1 Pa which is at least 300 cps, preferably 500 cps and a pearlescent agent, said pearlescent agent having D0.99 volume particle size of less than 60 μm.

15 Claims, No Drawings

OTHER PUBLICATIONS

U.S. Appl. No. 12/234,010, filed Sep. 19, 2008, Panandiker et al.
U.S. Appl. No. 12/235,110, filed Sep. 22, 2008, Panandiker et al.
U.S. Appl. No. 12/235,125, filed Sep. 22, 2008, Panandiker et al.
U.S. Appl. No. 12/235,140, filed Sep. 22, 2008, Panandiker et al.

* cited by examiner

LIQUID TREATMENT COMPOSITION

TECHNICAL FIELD

The present invention relates to the field of a liquid composition, preferably an aqueous composition, comprising a pearlescent agent and a rheology modifier capable of stably suspending the pearlescent agents.

BACKGROUND OF THE INVENTION

In the preparation of liquid treatment compositions, it is always an aim to improve technical capabilities thereof and aesthetics. The present invention specifically relates to the aim of improving on the traditional transparent or opaque aesthetics of liquid compositions. It is also an aim of the present invention to convey the composition's technical capabilities through the aesthetics of the composition. The present invention relates to liquid compositions comprising optical modifiers that are capable of transmitting light such that the compositions appear pearlescent.

Pearlescence can be achieved by incorporation and suspension of a pearlescent agent in the liquid composition. Pearlescent agents include inorganic natural substances, such as mica, bismuth oxychloride and titanium dioxide, and organic compounds such as fish scales, metal salts of higher fatty acids, fatty glycol esters and fatty acid alkanolamides. The pearlescent agent can be acquired as a powder, suspension of the agent in a suitable suspending agent or where the agent is a crystal, it may be produced in situ.

Pearlescent agents are particulate and tend to separate from the suspension or liquid composition over time. One solution to this problem is simply to increase the viscosity of the composition. However liquid laundry or hard surface cleaning compositions necessarily have relatively low viscosity, especially at high shear, such that they may be poured. Typically a laundry composition has viscosity of less than 1500 centipoises at 20 $s^{-1}$ and 21° C. Such products generally also have low viscosity at low shear, resulting in any particulates having a tendency to separate from the liquid composition and either float or settle upon storage. In either scenario this gives an undesired, non-uniform product appearance wherein part of the product is pearly and part of it is clear and homogeneous.

Another problem associated with the use of particulates, and especially pearlescent agents, in liquid laundry and hard surface cleaning applications is the likely deposition of the pearlescent agent on the surface being treated. On fabrics, especially dark fabrics, such deposits or residues can be visible with the naked eye. Moreover they may tend to draw the eye as, by their nature, they tend to sparkle in light. On dishware or hard surfaces, such as floors, deposits are equally as unappealing as they give the consumers the perception of the surface being dirty. With regard to dishware there is the added potentially issue that consumers may view the appearance of pearlescent agent on dishware as being a health issue.

Detergent compositions and pearlescent dispersions comprising pearlescent agent fatty acid glycol ester are disclosed in the following art; U.S. Pat. No. 4,717,501 (to Kao); U.S. Pat. No. 5,017,305 (to Henkel); U.S. Pat. No. 6,210,659 (to Henkel); U.S. Pat. No. 6,835,700 (to Cognis). Liquid detergent compositions containing pearlescent agent are disclosed in U.S. Pat. No. 6,956,017 (to Procter & Gamble). Liquid detergents for washing delicate garments containing pearlescent agent are disclosed in EP 520551 B1 (to Unilever).

In spite of the advances in the art, there remains a challenge to both stably suspend pearlescent agents in liquid laundry and hard surface cleaning treatment compositions and avoid the appearance of deposits or residues on the surface being treated.

SUMMARY OF THE INVENTION

According to the present invention there is provided a pearlescent liquid treatment composition suitable for use as a laundry or hard surface cleaning composition comprising a rheology modifier providing high shear viscosity at 20 $sec^{-1}$ at 21° C. of from 1 to 1500 cps and low shear viscosity at 0.05 $sec^{-1}$ at 21° C. of greater than 5000 cps. and a pearlescent agent, said pearlescent agent having D0.99 volume particle size of less than 50 μm.

According to an alternative embodiment of the present invention, there is provided a pearlescent liquid treatment composition suitable for use as a laundry or hard surface cleaning composition comprising a rheology modifier providing high shear viscosity at 20 $s^{-1}$ at 21 C of from 1 to 1500 cps and low shear viscosity at 0.05 $sec^{-1}$ at 21° C. of greater than 5000 cps. and a pearlescent agent, wherein the difference in refractive index ($\Delta N$) of the medium in which the pearlescent agent is suspended and the pearlescent agent is greater than 0.02.

DETAILED DESCRIPTION OF THE INVENTION

The liquid compositions of the present invention are suitable for use as laundry or hard surface cleaning treatment compositions. By the term laundry treatment composition it is meant to include all liquid compositions used in the treatment of laundry including cleaning and softening or conditioning compositions. By the term hard surface treatment compositions it is meant to include all liquid compositions used in the treatment of hard surfaces, such as kitchen or bathroom surfaces, as well as dish and cook ware in the hand or automatic dishwashing operations.

The compositions of the present invention are liquid, but may be packaged in a container or as an encapsulated and/or unitized dose. The latter form is described in more detail below. Liquid compositions may be aqueous or non-aqueous. Where the compositions are aqueous they may comprise from 2 to 90% water, more preferably from 20% to 80% water and most preferably from 25% to 65% water. Non-aqueous compositions comprise less than 12% water, preferably less than 10%, most preferably less than 9.5% water. Compositions used in unitized dose products comprising a liquid composition enveloped within a water-soluble film are often described to be non-aqueous. Compositions according to the present invention for this use comprise from 2% to 15% water, more preferably from 2% to 10% water and most preferably from 4% to 9% water.

The compositions of the present invention preferably have viscosity from 1 to 1500 centipoises (1-1500 mPa*s), more preferably from 100 to 1000 centipoises (100-1000 mPa*s), and most preferably from 200 to 500 centipoises (200-500 mPa*s) at 20 $s^{-1}$ and 21° C. Viscosity can be determined by conventional methods. Viscosity according to the present invention however is measured using an AR 550 rheometer from TA instruments using a plate steel spindle at 40 mm diameter and a gap size of 500 μm. The high shear viscosity at 20 $s^{-1}$ and low shear viscosity at 0.05-1 can be obtained from a logarithmic shear rate sweep from $0.1^{-1}$ to $25^{-1}$ in 3 minutes time at 21 C. The preferred rheology described therein may be achieved using internal existing structuring with detergent ingredients or by employing an external rheology modifier. More preferably laundry detergent liquid compositions have a high shear rate viscosity of from about 100 centipoise to 1500 centipoise, more preferably from 100 to 1000 cps. Unit Dose laundry detergent liquid compositions have high shear rate viscosity of from 400 to 1000 cps. Laundry softening compositions have high shear rate viscosity of from 10 to 1000, more preferably from 10 to 800 cps, most preferably from 10 to 500 cps. Hand dishwashing compositions have high shear rate viscosity of from 300 to 4000 cps, more preferably 300 to 1000 cps.

The composition to which the pearlescent agent is added is preferably transparent or translucent, but may be opaque. The compositions (before adding the pearlescent agent) preferably have an absolute turbidity of 5 to 3000 NTU as measured with a turbidity meter of the nephelometric type. Turbidity according to the present invention is measures using an Analyte NEP160 with probe NEP260 from McVan Instruments, Australia. In one embodiment of the present invention it has been found that even compositions with turbidity above 2800 NTU can be made pearlescent with the appropriate amount of pearlescent material. The Applicants have found however, that as turbidity of a composition is increased, light transmittance through the composition decreases. This decrease in light transmittance results in fewer of the pearlescent particles transmitting light, which further results in a decrease in pearlescent effect. The Applicants have thus found that this effect can to a certain extent be ameliorated by the addition of higher levels of pearlescent agent. However a threshold is reached at turbidity of 3000 NTU after which further addition of pearlescent agent does not improve the level of pearlescent effect.

The liquid of the present invention preferably has a pH of from 3 to 10, more preferably from 5 to 9, even more preferably from 6 to 9, most preferably from 7.1 to 8.5 when measured by dissolving the liquid to a level of 1% in demineralized water.

Pearlescent Agent

The pearlescent agents according to the present invention are crystalline or glassy solids, transparent or translucent compounds capable of reflecting and refracting light to produce a pearlescent effect. Typically, the pearlescent agents are crystalline particles insoluble in the composition in which they are incorporated. Preferably the pearlescent agents have the shape of thin plates or spheres. Spheres, according to the present invention, are to be interpreted as generally spherical. Particle size is measured across the largest diameter of the sphere. Plate-like particles are such that two dimensions of the particle (length and width) are at least 5 times the third dimension (depth or thickness). Other crystal shapes like cubes or needles or other crystal shapes do not display pearlescent effect. Many pearlescent agents like mica are natural minerals having monoclinic crystals. Shape appears to affect the stability of the agents. The spherical, even more preferably, the plate-like agents being the most successfully stabilised.

Pearlescent agents are known in the literature, but generally for use in shampoo, conditioner or personal cleansing applications. They are described as materials which impart, to a composition, the appearance of mother of pearl. The mechanism of pearlescence is described by R. L. Crombie in International Journal of Cosmetic Science Vol 19, page 205-214. Without wishing to be bound by theory, it is believed that pearlescence is produced by specular reflection of light as shown in the figure below. Light reflected from pearl platelets or spheres as they lie essentially parallel to each other at different levels in the composition creates a sense of depth and luster. Some light is reflected off the pearlescent agent, and the remainder will pass through the agent. Light passing through the pearlescent agent, may pass directly through or be refracted. Reflected, refracted light produces a different colour, brightness and luster.

The pearlescent agents preferably have D0.99 (sometimes referred to as D99) volume particle size of less than 50 μm. More preferably the pearlescent agents have D0.99 of less than 40 μm, most preferably less than 30 μm. Most preferably the particles have volume particle size greater than 1 μm. Most preferably the pearlescent agents have particle size distribution of from 0.1 μm to 50 μm, more preferably from 0.5 μm to 25 μm and most preferably from 1 μm to 20 μm. The D0.99 is a measure of particle size relating to particle size distribution and meaning in this instance that 99% of the particles have volume particle size of less than 50 μm. Volume particle size and particle size distribution are measured using the Hydro 2000G equipment available from Malvern Instruments Ltd. Particle size has a role in stabilization of the agents. The smaller the particle size and distribution, the more easily they are suspended. However as you decrease the particle size of the pearlescent agent, so you decrease the efficacy of the agent.

Without wishing to be bound by theory, the Applicant believes that the transmission of light at the interface of the pearlescent agent and the liquid medium in which it is suspended, is governed by the physical laws governed by the Fresnel equations. The proportion of light that will be reflected by the pearlescent agent increases as the difference in refractive index between the pearlescent agent and the liquid medium increases. The rest of the light will be refracted by virtue of the conservation of energy, and transmitted through the liquid medium until it meets another pearlescent agent surface. That being established, it is believed that the difference in refractive index must be sufficiently high so that sufficient light is reflected in proportion to the amount of light that is refracted in order for the composition containing the pearlescent agents to impart visual pearlescence.

Liquid compositions containing less water and more organic solvents will typically have a refractive index that is higher in comparison to more aqueous compositions. The Applicants have therefore found that in such compositions having a high refractive index, pearlescent agents with an insufficiently high refractive index do not impart sufficient visual pearlescence even when introduced at high level in the composition (typically more than 3%). It is therefore preferable to use a pearlescent pigment with a high refractive index in order to keep the level of pigment at a reasonably low level in the formulation. Hence the pearlescent agent is preferably chosen such that it has a refractive index of more than 1.41, more preferably more than 1.8, even more preferably more than 2.0. Preferably the difference in refractive index between the pearlescent agent and the composition or medium, to which pearlescent agent is then added, is at least 0.02. Preferably the difference in refractive index between the pearlescent agent and the composition is at least 0.2, more preferably at least 0.6. The Applicants have found that the higher the refractive index of the agent the more effective is the agent in producing pearlescent effect. This effect however is also dependent on the difference in refractive index of the agent and of the composition. The greater the difference the greater is the perception of the effect.

The liquid compositions of the present invention preferably comprise from 0.01% to 2.0% by weight of the composition of a 100% active pearlescent agent. More preferably the liquid composition comprises from 0.01% to 0.5%, more preferably from 0.01% 0.35%, even more preferably from 0.01% to 0.2% by weight of the composition of the 100% active pearlescent agents. The Applicants have found that in spite of the above mentioned particle size and level in composition, it is possible to deliver good, and consumer preferred, pearlescence to the liquid composition.

The pearlescent agents may be organic or inorganic.

Organic Pearlescent Agents:

Suitable pearlescent agents include monoester and/or diester of alkylene glycols having the formula:

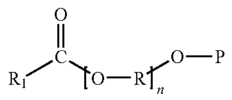

wherein $R_1$ is linear or branched C12-C22 alkyl group;

R is linear or branched C2-C4 alkylene group;

P is selected from H, C1-C4 alkyl or —$COR_2$, $R_2$ is C4-C22 alkyl, preferably C12-C22 alkyl; and n=1-3.

In one embodiment of the present invention, the long chain fatty ester has the general structure described above, wherein $R_1$ is linear or branched C16-C22 alkyl group, R is —$CH_2$—$CH_2$—, and P is selected from H, or —$COR_2$, wherein $R_2$ is C4-C22 alkyl, preferably C12-C22 alkyl.

Typical examples are monoesters and/or diesters of ethylene glycol, propylene glycol, diethylene glycol, dipropylene glycol, triethylene glycol or tetraethylene glycol with fatty acids containing from about 6 to about 22, preferably from about 12 to about 18 carbon atoms, such as caproic acid, caprylic acid, 2-ethyhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid, erucic acid, and mixtures thereof.

In one embodiment, ethylene glycol monostearate (EGMS) and/or ethylene glycol distearate (EGDS) and/or polyethylene glycol monostearate (PGMS) and/or polyethyleneglycol distearate (PGDS) are the pearlescent agents used in the composition. There are several commercial sources for these materials. For Example, PEG6000MS® is available from Stepan, Empilan EGDS/A® is available from Albright & Wilson.

In another embodiment, the pearlescent agent comprises a mixture of ethylene glycol diester/ethylene glycol monoester having the weight ratio of about 1:2 to about 2:1. In another embodiment, the pearlescent agent comprising a mixture of EGDS/EGMS having the weight ratio of bout 60:40 to about 50:50 is found to be particularly stable in water suspension.

Co-Crystallizing Agents:

Optionally, co-crystallizing agents are used to enhance the crystallization of the organic pearlescent agents such that pearlescent particles are produced in the resulting product. Suitable co-crystallizing agents include but are not limited to fatty acids and/or fatty alcohols having a linear or branched, optionally hydroxyl substituted, alkyl group containing from about 12 to about 22, preferably from about 16 to about 22, and more preferably from about 18 to 20 carbon atoms, such as palmitic acid, linoleic acid, stearic acid, oleic acid, ricinoleic acid, behenyl acid, cetearyl alcohol, hydroxystearyl alcohol, behenyl alcohol, linolyl alcohol, linolenyl alcohol, and mixtures thereof.

When the co-crystallizing agents are selected to have a higher melting point than the organic pearlescent agents, it is found that in a molten mixture of these co-crystallizing agents and the above organic pearlescent agents, the co-crystallizing agents typically solidify first to form evenly distributed particulates, which serve as nuclei for the subsequent crystallization of the pearlescent agents. With a proper selection of the ratio between the organic pearlescent agent and the co-crystallizing agent, the resulting crystals sizes can be controlled to enhance the pearlescent appearance of the resulting product. It is found that if too much co-crystallizing agent is used, the resulting product exhibits less of the attractive pearlescent appearance and more of an opaque appearance.

In one embodiment where the co-crystallizing agent is present, the composition comprises 1-5 wt % C12-C20 fatty acid, C12-C20 fatty alcohol, or mixtures thereof.

In another embodiment, the weight ratio between the organic pearlescent agent and the co-crystallizing agent ranges from about 3:1 to about 10:1, or from about 5:1 to about 20:1.

One of the widely employed methods to produce organic pearlescent agent containing compositions is a method using organic pearlescent materials that are solid at room temperature. These materials are heated to above their melting points and added to the preparation of composition; upon cooling, a pearlescent luster appears in the resulting composition. This method however can have disadvantages as the entire production batch must be heated to a temperature corresponding to the melting temperature of the pearlescent material, and uniform pearlescence in the product is achieved only by making a homogeneous molten mixture and applying well controlled cooling and stirring conditions.

An alternative, and preferred method of incorporating organic pearlescent agents into a composition is to use a pre-crystallized organic pearlescent dispersion. This method is known to those skilled in the art as "cold pearl". In this alternative method, the long chain fatty esters are melted, combined with a carrier mixture and recrystallized to an optimum particle size in a carrier. The carrier mixture typically comprises surfactant, preferably from 2-50% surfactant, and the balance of water and optional adjuncts. Pearlescent crystals of a defined size are obtainable by the proper choices of surfactant carrier mixture, mixing and cooling conditions. The process of making cold pearls are described on U.S. Pat. Nos. 4,620,976, 4,654,163 (both assigned to Hoechest) and WO2004/028676 (assigned to Huntsman International). A number of cold pearls are commercially available. These include trade names such as Stepan, Pearl-2 and Stepan Pearl 4 (produced by Stepan Company Northfield, Ill.), Mackpearl 202, Mackpearl 15-DS, Mackpearl DR-104, Mackpearl DR-106 (all produced by McIntyre Group, Chicago, Ill.), Euperlan PK900 Benz-W and Euperlan PK 3000 AM (produced by Cognis Corp).

A typical embodiment of the invention incorporating an organic pearlescent agent is a composition comprising from 0.1% to 5% by weight of composition of the organic pearlescent agent, from 0.5% to 10% by weight of the composition of a dispersing surfactant, and optionally, an effective amount of a co-crystallizing agent in a solvent system comprising water and optionally one or more organic solvents, in addition, from 5% to 40% by weight of the composition, of a detersive surfactant, and at least 0.01%, preferably at least 1% by weight of the composition, of one or more laundry adjunct materials such as perfume, fabric softener, enzyme, bleach, bleach activator, coupling agent, or combinations thereof.

The "effective amount" of co-crystallizing agent is the amount sufficient to produce the desired crystal size and size distribution of the pearlescent agents, under a given set processing parameters. In some embodiments, the amount of co-crystallizing agent ranges from 5 to 30 parts, per 100 weight parts organic pearlescent agent.

Suitable dispersing surfactants for cold pearls include alkyl sulfates, alkyl ether sulfates, and mixtures thereof, wherein the alkyl group is linear or branched C12-C14 alkyls. Typical examples include but are not limited to sodium lauryl sulfate and ammonium lauryl sulfate.

In one embodiment of the present invention, the composition comprises 20-65 wt % water; 5-25 wt % sodium alkyl sulfate alkyl sulfate or alkyl ether sulfate dispersing surfactant; and 0.5-15 wt % ethylene glycol monostearate and ethylene glycol distearate in the weight ratio of 1:2 to 2:1.

In another embodiment of the present invention, the composition comprises 20-65 wt % water; 5-30 wt % sodium alkyl sulfate or alkyl ether sulfate dispersing surfactant; 5-30 wt % long chain fatty ester and 1-5 wt % C12-C22 fatty alcohol or fatty acid, wherein the weight ratio of long chain fatty ester to fatty alcohol and/or fatty acid ranges from about 5:1 to about 20:1, or from about 3:1 to about 10:1.

In another embodiment of the invention, the composition comprises at least about 0.01%, preferably from about 0.01% to about 5% by weight of the composition of the pearlescent agents, an effective amount of the co-crystallizing agent and one or more of the following: a detersive surfactant; a fixing agent for anionic dyes; a solvent system comprising water and an organic solvent. This composition can further include other laundry and fabric care adjuncts.

Production Process for Incorporating Organic Pearlescent Agents:

The cold pearl is produced by heating the a carrier comprised of 2-50% surfactant, balance water and other adjuncts to a temperature above the melting point of the organic pearlescent agent and co-crystallizing agent, typically from about 60-90° C., preferably about 75-80° C. The organic pearlescent agent and the co-crystallizing agent are added to the mixture and mixed for about 10 minutes to about 3 hours. Optionally, the temperature is then raised to about 80-90° C. A high shear mill device may be used to produce the desired dispersion droplet size of the pearlescent agent.

The mixture is cooled down at a cooling rate of about 0.5-5° C./min. Alternatively, cooling is carried out in a two-step process, which comprises an instantaneous cooling step by passing the mixture through a single pass heat exchanger and a slow cooling step wherein the mixture is cooled at a rate of about 0.5-5° C./min. Crystallization of the pearlescent agent such as a long chain fatty ester starts when the temperature reaches about 50° C.; the crystallization is evidenced by a substantial increase in the viscosity of the mixture. The mixture is cooled down to about 30° C. and the stirring is stopped.

The resulting cold pearl precrystallised organic pearlescent dispersion can subsequently be incorporated into the liquid composition with stirring and without any externally applied heat. The resulting product has an attractive pearlescent appearance and is stable for months under typical storage conditions. In other words, the resulting product maintains its pearlescent appearance and the cold pearl does not exhibit separation or stratification from the composition matrix for months.

Inorganic Pearlescent Agents

Inorganic pearlescent agents include those selected from the group consisting of mica, metal oxide coated mica, silica coated mica, bismuth oxychloride coated mica, bismuth oxychloride, myristyl myristate, glass, metal oxide coated glass, guanine, glitter (polyester or metallic) and mixtures thereof.

Suitable micas includes muscovite or potassium aluminum hydroxide fluoride. The platelets of mica are preferably coated with a thin layer of metal oxide. Preferred metal oxides are selected from the group consisting of rutile, titanium dioxide, ferric oxide, tin oxide, alumina and mixtures thereof. The crystalline pearlescent layer is formed by calcining mica coated with a metal oxide at about 732° C. The heat creates an inert pigment that is insoluble in resins, has a stable color, and withstands the thermal stress of subsequent processing Color in these pearlescent agents develops through interference between light rays reflecting at specular angles from the top and bottom surfaces of the metal-oxide layer. The agents lose color intensity as viewing angle shifts to non-specular angles and gives it the pearlscent appearance.

More preferably inorganic pearlescent agents are selected from the group consisting of mica and bismuth oxychloride and mixtures thereof. Most preferably inorganic pearlescent agents are mica. Commercially available suitable inorganic pearlescent agents are available from Merck under the tradenames Iriodin, Biron, Xirona, Timiron Colorona, Dichrona, Candurin and Ronastar. Other commercially available inorganic pearlescent agent are available from BASF (Engelhard, Mearl) under tradenames Biju, Bi-Lite, Chroma-Lite, Pearl-Glo, Mearlite and Eckart under the tradenames Prestige Soft Silver and Prestige Silk Silver Star.

Organic pearlescent agent such as ethylene glycol mono stearate and ethylene glycol distearate provide pearlescence, but only when the composition is in motion. Hence only when the composition is poured will the composition exhibit pearlescence. Inorganic pearlescent materials are preferred as the provide both dynamic and static pearlescence. By dynamic pearlescence it is meant that the composition exhibits a pearlescent effect when the composition is in motion. By static pearlescence it is meant that the composition exhibits pearlescence when the composition is static.

Inorganic pearlescent agents are available as a powder, or as a slurry of the powder in an appropriate suspending agent. Suitable suspending agents include ethylhexyl hydroxystearate, hydrogenated castor oil. The powder or slurry of the powder can be added to the composition without the need for any additional process steps.

Rheology Modifier

In a preferred embodiment of the present invention, the composition comprises a rheology modifier. The rheology modifier is selected from the group consisting of non-polymeric crystalline, hydroxy-functional materials, polymeric rheology modifiers which impart shear thinning characteristics to the aqueous liquid matrix of the composition. Such rheology modifiers are preferably those which impart to the aqueous liquid composition a high shear viscosity at 20 $sec^{-1}$ at 21° C. of from 1 to 1500 cps and a viscosity at low shear (0.05 $sec^{-1}$ at 21° C.) of greater than 5000 cps. Viscosity according to the present invention is measured using an AR 550 rheometer from TA instruments using a plate steel spindle at 40 mm diameter and a gap size of 500 μm. The high shear viscosity at 20 $s^{-1}$ and low shear viscosity at 0.5-1 can be obtained from a logarithmic shear rate sweep from $0.1^{-1}$ to $25^{-1}$ in 3 minutes time at 21 C. Crystalline, hydroxy-functional materials are rheology modifiers which form thread-like structuring systems throughout the matrix of the composition upon in situ crystallization in the matrix. Polymeric rheology modifiers are preferably selected from polyacrylates, polymeric gums, other non-gum polysaccharides, and combinations of these polymeric materials.

The overall objective in adding such a rheology modifier to the compositions herein is to arrive at liquid compositions which are suitably functional and aesthetically pleasing from the standpoint of product thickness, product pourability, product optical properties, and/or particles suspension performance. Thus the rheology modifier will generally serve to establish appropriate rheological characteristics of the liquid product and will do so without imparting any undesirable attributes to the product such as unacceptable optical properties or unwanted phase separation. Generally the rheology modifier will comprise from 0.01% to 1% by weight, preferably from 0.05% to 0.75% by weight, more preferably from 0.1% to 0.5% by weight, of the compositions herein.

The rheology modifier component of the compositions herein can be characterized as an "external" or "internal" rheology modifier. Preferably the rheology modifier of the present invention is an external rheology modifier. An "external" rheology modifier, for purposes of this invention, is a material which has as its primary function that of providing rheological alteration of the liquid matrix. Generally, therefore, an external rheology modifier will not, in and of itself, provide any significant fabric cleaning or fabric care benefit or any significant ingredient solubilization benefit. An external rheology modifier is thus distinct from an "internal" rheology modifier which may also alter matrix rheology but which has been incorporated into the liquid product for some additional primary purpose. Thus, for example, a preferred internal rheology modifier would be anionic surfactants which can serve to alter rheological properties of liquid detergents, but which have been added to the product primarily to act as the cleaning ingredient.

The external rheology modifier of the compositions of the present invention is used to provide an aqueous liquid matrix for the composition which has certain rheological characteristics. The principal one of these characteristics is that the matrix must be "shear-thinning". A shear-thinning fluid is one with a viscosity which decreases as shear is applied to the fluid. Thus, at rest, i.e., during storage or shipping of the liquid detergent product, the liquid matrix of the composition should have a relatively high viscosity. When shear is applied to the composition, however, such as in the act of pouring or squeezing the composition from its container, the viscosity of the matrix should be lowered to the extent that dispensing of the fluid product is easily and readily accomplished.

The at-rest viscosity of the compositions herein will ideally be high enough to accomplish several purposes. Chief among these purposes is that the composition at rest should be sufficiently viscous to suitably suspend the pearlescent, another essential component of the invention herein. A secondary benefit of a relatively high at-rest viscosity is an aesthetic one of giving the composition the appearance of a thick, strong, effective product as opposed to a thin, weak, watery one. Finally, the requisite rheological characteristics of the liquid matrix should be provided via an external rheology modifier which does not disadvantageously detract from the visibility of the aesthetic agent suspended within the composition, i.e., by making the matrix opaque to the extent that the suspended obscured. aesthetic agent is obscured.

Materials which form shear-thinning fluids when combined with water or other aqueous liquids are generally known in the art. Such materials can be selected for use in the compositions herein provided they can be used to form an aqueous liquid matrix having the rheological characteristics set forth hereinbefore.

One type of structuring agent which is especially useful in the compositions of the present invention comprises non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. Such materials will generally be selected from those having the following formulas:

I)

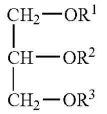 wherein: $R^1$ is 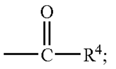

$R^2$ is $R^1$ or H;

$R^3$ is $R^1$ or H;

$R^4$ is independently $C_{10}$-$C_{22}$ alkyl or alkenyl comprising at least one hydroxyl group;

II)

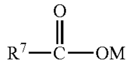 wherein: $R^7$ is 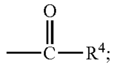

$R^4$ is as defined above in i);

M is $Na^+$, $K^+$, $Mg^{++}$ or $Al^{3+}$, or H; and

Z—(CH(OH))a-Z' III)

where a is from 2 to 4, preferably 2; Z and Z' are hydrophobic groups, especially selected from $C_6$-$C_{20}$ alkyl or cycloalkyl, $C_6$-$C_{24}$ alkaryl or aralkyl, $C_6$-$C_{20}$ aryl or mixtures thereof. Optionally Z can contain one or more nonpolar oxygen atoms as in ethers or esters.

Materials of the Formula I type are preferred. They can be more particularly defined by the following formula:

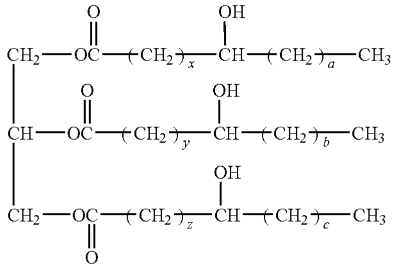

wherein:

(x+a) is from between 11 and 17;

(y+b) is from between 11 and 17; and (z+c) is from between 11 and 17.

Preferably, in this formula x=y=z=10 and/or a=b=c=5.

Specific examples of preferred crystalline, hydroxyl-containing rheology modifiers include castor oil and its derivatives. Especially preferred are hydrogenated castor oil derivatives such as hydrogenated castor oil and hydrogenated castor wax. Commercially available, castor oil-based, crystalline, hydroxyl-containing rheology modifiers include THIXCIN® from Rheox, Inc. (now Elementis).

Alternative commercially available materials that are suitable for use as crystalline, hydroxyl-containing rheology modifiers are those of Formula III hereinbefore. An example of a rheology modifier of this type is 1,4-di-O-benzyl-D-Threitol in the R,R, and S,S forms and any mixtures, optically active or not.

All of these crystalline, hydroxyl-containing rheology modifiers as hereinbefore described are believed to function by forming thread-like structuring systems when they are crystallized in situ within the aqueous liquid matrix of the compositions herein or within a pre-mix which is used to form such an aqueous liquid matrix. Such crystallization is brought about by heating an aqueous mixture of these materials to a temperature above the melting point of the rheology modifier, followed by cooling of the mixture to room temperature while maintaining the liquid under agitation.

Under certain conditions, the crystalline, hydroxyl-containing rheology modifiers will, upon cooling, form the thread-like structuring system within the aqueous liquid matrix. This thread-like system can comprise a fibrous or entangled thread-like network. Non-fibrous particles in the form of "rosettas" may also be formed. The particles in this network can have an aspect ratio of from 1.5:1 to 200:1, more preferably from 10:1 to 200:1. Such fibers and non-fibrous particles can have a minor dimension which ranges from 1 micron to 100 microns, more preferably from 5 microns to 15 microns.

These crystalline, hydroxyl-containing materials are especially preferred rheology modifiers for providing the detergent compositions herein with shear-thinning rheology. They can effectively be used for this purpose at concentrations which are low enough that the compositions are not rendered so undesirably opaque that bead visibility is restricted. These materials and the networks they form also serve to stabilize the compositions herein against liquid-liquid or solid-liquid (except, of course, for the beads and the structuring system particles) phase separation. Their use thus permits the formulator to use less of relatively expensive non-aqueous solvents or phase stabilizers which might otherwise have to be used in higher concentrations to minimize undesirable phase separation. These preferred crystalline, hydroxyl-containing rheology modifiers, and their incorporation into aqueous shear-thinning matrices, are described in greater detail in U.S. Pat. No. 6,080,708 and in PCT Publication No. WO 02/40627.

Other types of rheology modifiers, besides the non-polymeric, crystalline, hydroxyl-containing rheology modifiers described hereinbefore, may be utilized in the liquid detergent compositions herein. Polymeric materials which will provide shear-thinning characteristics to the aqueous liquid matrix may also be employed.

Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum.

If polymeric rheology modifiers are employed herein, a preferred material of this type is gellan gum. Gellan gum is a heteropolysaccharide prepared by fermentation of Pseudomonaselodea ATCC 31461. Gellan gum is commercially marketed by CP Kelco U.S., Inc. under the KELCOGEL tradename. Processes for preparing gellan gum are described in U.S. Pat. Nos. 4,326,052; 4,326,053; 4,377,636 and 4,385,123.

A further alternative and suitable rheology modifier is a combination of a solvent and a polycarboxylate polymer. More specifically the solvent is preferably an alkylene glycol. More preferably the solvent is dipropy glycol. Preferably the polycarboxylate polymer is a polyacrylate, polymethacrylate or mixtures thereof. The solvent is preferably present at a level of from 0.5 to 15%, preferably from 2 to 9% of the composition. The polycarboxylate polymer is preferably present at a level of from 0.1 to 10%, more preferably 2 to 5% of the composition. The solvent component preferably comprises a mixture of dipropykeneglycol and 1,2-propanediol. The ratio of dipropyleneglycol to 1,2-propanediol is preferably 3:1 to 1:3, more preferably 1:1. The polyacrylate is preferably a copolymer of unsaturated mono- or di-carbonic acid and 1-30 C alkyl ester of the (meth) acrylic acid. In another preferred embodiment the rheology modifier is a polyacrylate of unsaturated mono- or di-carbonic acid and 1-30 C alkyl ester of the (meth) acrylic acid. Such copolymers are available from Noveon Inc under the tradename Carbopol Aqua 30.

Of course, any other rheology modifiers besides the foregoing specifically described materials can be employed in the aqueous liquid detergent compositions herein, provided such other rheology modifier materials produce compositions having the selected rheological characteristics hereinbefore described. Also combinations of various rheology modifiers and rheology modifier types may be utilized, again so long as the resulting aqueous matrix of the composition possesses the hereinbefore specified pour viscosity, constant stress viscosity and viscosity ratio values.

Optional Composition Ingredients

The liquid compositions of the present invention may comprise other ingredients selected from the list of optional ingredients set out below. Unless specified herein below, an "effective amount" of a particular laundry adjunct is preferably from 0.01%, more preferably from 0.1%, even more preferably from 1% to 20%, more preferably to 15%, even more preferably to 10%, still even more preferably to 7%, most preferably to 5% by weight of the detergent compositions.

Surfactants or Detersive Surfactants

The compositions of the present invention may comprise from about 1% to 80% by weight of a surfactant. Preferably such compositions comprise from about 5% to 50% by weight of surfactant. Surfactants of the present invention may be used in 2 ways. Firstly they may be used as a dispersing agent for the cold pearl organic pearlescent agents as described above. Secondly they may be used as detersive surfactants for soil suspension purposes.

Detersive surfactants utilized can be of the anionic, nonionic, zwitterionic, ampholytic or cationic type or can comprise compatible mixtures of these types. More preferably surfactants are selected from the group consisting of anionic, nonionic, cationic surfactants and mixtures thereof. Preferably the compositions are substantially free of betaine surfactants. Detergent surfactants useful herein are described in U.S. Pat. No. 3,664,961, Norris, issued May 23, 1972, U.S. Pat. No. 3,919,678, Laughlin et al., issued Dec. 30, 1975, U.S. Pat. No. 4,222,905, Cockrell, issued Sep. 16, 1980, and in U.S. Pat. No. 4,239,659, Murphy, issued Dec. 16, 1980. Anionic and nonionic surfactants are preferred.

Useful anionic surfactants can themselves be of several different types. For example, water-soluble salts of the higher fatty acids, i.e., "soaps", are useful anionic surfactants in the compositions herein. This includes alkali metal soaps such as the sodium, potassium, ammonium, and alkyl ammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Additional non-soap anionic surfactants which are suitable for use herein include the water-soluble salts, preferably the alkali metal, and ammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are a) the sodium, potassium and ammonium alkyl sulfates, especially those obtained by sulfating the higher alcohols ($C_8$-$C_{18}$ carbon atoms) such as those produced by reducing the glycerides of tallow or coconut oil; b) the sodium, potassium and ammonium alkyl polyethoxylate sulfates, particularly those in which the alkyl group contains from 10 to 22, preferably from 12 to 18 carbon atoms, and wherein the polyethoxylate chain contains from 1 to 15, preferably 1 to 6 ethoxylate moieties; and c) the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11}$-$C_{13}$ LAS.

Preferred nonionic surfactants are those of the formula $R^1(OC_2H_4)_nOH$, wherein $R^1$ is a $C_{10}$-$C_{16}$ alkyl group or a $C_8$-$C_{12}$ alkyl phenyl group, and n is from 3 to about 80. Particularly preferred are condensation products of $C_{12}$-$C_{15}$ alcohols with from about 5 to about 20 moles of ethylene oxide per mole of alcohol, e.g., $C_{12}$-$C_{13}$ alcohol condensed with about 6.5 moles of ethylene oxide per mole of alcohol.

Fabric Care Benefit Agents

According to a preferred embodiment of the compositions herein there is comprised a fabric care benefit agent. As used herein, "fabric care benefit agent" refers to any material that can provide fabric care benefits such as fabric softening, color protection, pill/fuzz reduction, anti-abrasion, anti-wrinkle, and the like to garments and fabrics, particularly on cotton and cotton-rich garments and fabrics, when an adequate amount of the material is present on the garment/fabric. Non-limiting examples of fabric care benefit agents include cationic surfactants, silicones, polyolefin waxes, latexes, oily sugar derivatives, cationic polysaccharides, polyurethanes, fatty acids and mixtures thereof. Fabric care benefit agents when present in the composition, are suitably at levels of up to about 30% by weight of the composition, more typically from about 1% to about 20%, preferably from about 2% to about 10% in certain embodiments.

For the purposes of the present invention, silicone derivatives are any silicone materials which can deliver fabric care benefits and can be incorporated into a liquid treatment composition as an emulsion, latex, dispersion, suspension and the like. In laundry products these are most commonly incorporated with suitable surfactants. Any neat silicones that can be directly emulsified or dispersed into laundry products are also covered in the present invention since laundry products typically contain a number of different surfactants that can behave like emulsifiers, dispersing agents, suspension agents, etc. thereby aiding in the emulsification, dispersion, and/or suspension of the water insoluble silicone derivative. By depositing on the fabrics, these silicone derivatives can provide one or more fabric care benefit to the fabric including anti-wrinkle, color protection, pill/fuzz reduction, anti-abrasion, fabric softening and the like. Examples of silicones useful in this invention are described in "Silicones—Fields of Application and Technology Trends" by Yoshiaki Ono, Shin-Etsu Silicones Ltd, Japan and by M. D. Berthiaume in Principles of Polymer Science and Technology in Cosmetics and Personal Care (1999).

Suitable silicones include silicone fluids such as poly(di)alkyl siloxanes, especially polydimethyl siloxanes and cyclic silicones. Poly(di)alkylsiloxanes may be branched, partially crosslinked or linear and with the following structure:

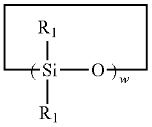

or

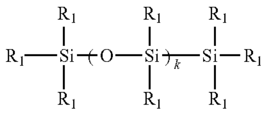

Where each $R_1$ is independently selected from H, linear, branched and cyclic alkyl and groups having 1-20 carbon atoms, linear, branched and cyclic alkenyl groups having 2-20 carbon atoms, alkylaryl and arylalkenyl groups with 7-20 carbon atoms, alkoxy groups having 1-20 carbon atoms, hydroxy and combinations thereof, w is selected from 3-10 and k from 2-10,000.

The polydimethylsiloxane derivatives of the present invention include, but are not limited to organofunctional silicones.

One embodiment of functional silicone are the ABn type silicones disclosed in U.S. Pat. Nos. 6,903,061B2, 6,833,344 and WO-02/018528. Commercially available examples of these silicones are Waro and Silsoft 843, both sold by GE Silicones, Wilton, Conn.

Another embodiment of functionalized silicones is the group of silicones with general formula (I)

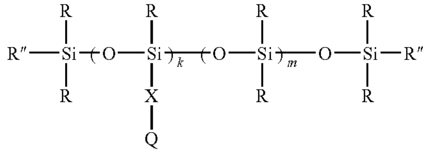

wherein:

(a) each R" is independently selected from R and —X-Q; wherein:

(i) R is a group selected from: a $C_1$-$C_8$ alkyl or aryl group, hydrogen, a $C_1$-$C_3$ alkoxy or combinations thereof;

(b) X is a linking group selected from: an alkylene group $—(CH_2)_p—$; or $—CH_2—CH(OH)—CH_2—$; wherein:

(i) p is from 2 to 6, (c) Q is $—(O—CHR_2—CH_2)_q—Z$; wherein q is on average from about 2 to about 20; and further wherein:

(i) $R_2$ is a group selected from: H; a $C_1$-$C_3$ alkyl; and (ii) Z is a group selected from: $—OR_3$; $—OC(O)R_3$; $—CO—R_4—COOH$; $—SO_3$; $—PO(OH)_2$;

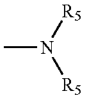

wherein:

$R_3$ is a group selected from: H; $C_1$-$C_{26}$ alkyl or substituted alkyl; $C_6$-$C_{26}$ aryl or substituted aryl;

$C_7$-$C_{26}$ alkylaryl or substituted alkylaryl; in some embodiments, $R_3$ is a group selected from: H; methyl; ethyl propyl; or benzyl groups;

$R_4$ is a group selected from: $—CH_2—$; or $—CH_2CH_2—$;

$R_5$ is a group independently selected from: H, $C_1$-$C_3$ alkyl; $—(CH_2)_p—NH_2$; and $—X(—O—CHR_2—CH_2)_q—Z$;

(d) k is on average from about 1 to about 25,000, or from about 3 to about 12,000; and (e) m is on average from about 4 to about 50,000, or from about 10 to about 20,000.

Examples of functionalized silicones included in the present invention are silicone polyethers, alkyl silicones, phenyl silicones, aminosillicones, silicone resins, silicone mercaptans, cationic silicones and the like.

Functionalized silicones or copolymers with one or more different types of functional groups such as amino, alkoxy, alkyl, phenyl, polyether, acrylate, silicon hydride, mercaptoproyl, carboxylic acid, quaternized nitrogen. Non-limiting examples of commercially available silicone include SM2125, Silwet 7622, commercially available from GE Silicones, and DC8822 and PP-5495, and DC-5562, all of which are commercially available from Dow Corning. Other examples include KF-888, KF-889, both of which are available from Shin Etsu Silicones, Akron, Ohio; Ultrasil® SW-12, Ultrasil® DW-18, Ultrasil® DW-AV, Ultrasil® Q-Plus, Ultrasil® Ca-1, Ultrasil® CA-2, Ultrasil® SA-1 and Ultrasil® PE-100 all available from Noveon Inc., Cleveland, Ohio. Additional non-limiting examples include Pecosil® CA-20, Pecosil® SM-40, Pecosil® PAN-150 available from Phoenix Chemical Inc., of Somerville.

In terms of silicone emulsions, the particle size can be in the range from about 1 nm to 100 microns and preferably from about 10 nm to about 10 microns including microemulsions (<150 nm), standard emulsions (about 200 nm to about 500 nm) and macroemulsions (about 1 micron to about 20 microns).

The oily sugar derivatives suitable for use in the present invention are taught in WO 98/16538. In context of the present invention, the initials CPE or RSE stand for a cyclic polyol derivatives or a reduced saccharide derivative respectively which result from 35% to 100% of the hydroxyl group of the cyclic polyol or reduced saccharide being esterified and/or etherified and in which at least two or more ester or ether groups are independently attached to a C8 to C22 alkyl or alkenyl chain. Typically CPE's and RSE's have 3 or more ester or ether groups or mixtures thereof. It is preferred if two or more ester or ether groups of the CPE and RSE are independently attached to a C8 to C22 alkyl or alkenyl chain. The C8 to C22 alkyl or alkenyl chain may be linear or branched. In one embodiment 40 to 100% of the hydroxyl groups are esterified or etherified. In another embodiment, 50% to 100% of the hydroxyl groups are esterified or etherified.

In the context of the present invention, the term cyclic polyol encompasses all forms of saccharides. Especially preferred are the CPEs and RSEs from monosaccharides and disaccharides. Examples of monosaccharides include xylose, arabinose, galactose, fructose, and glucose. Example of reduced saccharide is sorbitan. Examples of disaccharides are sucrose, lactose, maltose and cellobiose. Sucrose is especially preferred.

It is preferred if the CPEs or RSEs have 4 or more ester or ether groups. If the cyclic CPE is a disaccharide, it is preferred that disaccharide has three or more ester or ether groups. Particularly preferred are sucrose esters with 4 or more ester groups. These are commercially available under the trade name Olean from Procter and Gamble Company, Cincinnati Ohio.

If cyclic polyol is a reducing sugar, it is advantageous if the ring of the CPE has one ether group, preferably at Cl position. The remaining hydroxyl groups are esterified with alkyl groups.

All dispersible polyolefins that provide fabric care benefits can be used as the water insoluble fabric care benefit agents according to the present invention. The polyolefins can be in the form of waxes, emulsions, dispersions or suspensions. Non-limiting examples are discussed below.

Preferably, the polyolefin is a polyethylene, polypropylene, or a mixture thereof. The polyolefin may be at least partially modified to contain various functional groups, such as carboxyl, alkylamide, sulfonic acid or amide groups. More preferably, the polyolefin employed in the present invention is at least partially carboxyl modified or, in other words, oxidized. In particular, oxidized or carboxyl modified polyethylene is preferred in the compositions of the present invention.

For ease of formulation, the dispersible polyolefin is preferably introduced as a suspension or an emulsion of polyolefin dispersed by use of an emulsifying agent. The polyolefin suspension or emulsion preferably comprises from about 1% to about 60%, more preferably from about 10% to about 55%, and most preferably from about 20 to about 50% by weight of polyolefin. The polyolefin preferably has a wax dropping point (see ASTM D3954-94, volume 15.04—"Standard Test Method for propping Point of Waxes", the method incorporated herein by reference) from about 20 to 170° C. and more preferably from about 50 to 140° C. Suitable polyethylene waxes are available commercially from suppliers including but not limited to Honeywell (A-C polyethylene), Clariant (Velustrol emulsion), and BASF (LUWAX).

When an emulsion is employed, the emulsifier may be any suitable emulsification agent including anionic, cationic, or nonionic surfactants, or mixtures thereof. Almost any suitable surfactant may be employed as the emulsifier of the present invention. The dispersible polyolefin is dispersed by use of an emulsifier or suspending agent in a ratio 1:100 to about 1:2. Preferably, the ratio ranges from about 1:50 to 1:5.

Polymer latex is typically made by an emulsion polymerization process which includes one or more monomers, one or more emulsifiers, an initiator, and other components familiar to those of ordinary skill in the art. All polymer latexes that provide fabric care benefits can be used as water insoluble fabric care benefit agents of the present invention. Non-limiting examples of suitable polymer latexes include those disclosed in WO 02/018451 published in the name of Rhodia Chimie. Additional non-limiting examples include the monomers used in producing polymer latexes such as:

1) 100% or pure butylacrylate
2) Butylacrylate and butadiene mixtures with at least 20% (weight monomer ratio) of butylacrylate
3) Butylacrylate and less than 20% (weight monomer ratio) of other monomers excluding butadiene
4) Alkylacrylate with an alkyl carbon chain at or greater than C6
5) Alkylacrylate with an alkyl carbon chain at or greater than C6 and less than 50% (weight monomer ratio) of other monomers
6) A third monomer (less than 20% weight monomer ratio) added into monomer systems from 1) to 5)

Polymer latexes that are suitable fabric care benefit agents in the present invention include those having a glass transition temperature of from about −120° C. to about 120° C. and preferably from about −80° C. to about 60° C. Suitable emulsifiers include anionic, cationic, nonionic and amphoteric surfactants. Suitable initiators include all initiators that are suitable for emulsion polymerization of polymer latexes. The particle size of the polymer latexes can be from about 1 nm to about 10 μm and is preferably from about 10 nm to about 1 μm.

Cationic surfactants are another class of care actives useful in this invention. Examples of cationic surfactants having the formula

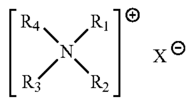

have been disclosed in US2005/0164905, wherein $R_1$ and $R_2$ are individually selected from the group consisting of $C_1$-$C_4$ alkyl, $C_1$-$C_4$ hydroxy alkyl, benzyl, and —$(C_nH_{2n}O)_xH$ where x has a value from 2 to 5; and n has a value of 1-4; X is an anion;

$R_3$ and $R_4$ are each a $C_8$-$C_{22}$ alkyl or (2) $R_3$ is a $C_8$-$C_{22}$ alkyl and $R_4$ is selected from the group consisting of $C_1$-$C_{10}$ alkyl, $C_1$-$C_{10}$ hydroxy alkyl, benzyl, —$(C_nH_{2n}O)_xH$ where x has a value from 2 to 5; and n has a value of 1-4.

Another preferred fabric care benefit agent is a fatty acid. When deposited on fabrics, fatty acids or soaps thereof, will provide fabric care (softness, shape retention) to laundry fabrics. Useful fatty acids (or soaps=alkali metal soaps such as the sodium, potassium, ammonium, and alkyl ammonium salts of fatty acids) are the higher fatty acids containing from about 8 to about 24 carbon atoms, more preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap. Fatty acids can be from natural or synthetic origin, both saturated and unsaturated with linear or branched chains.

Detersive Enzymes

Suitable detersive enzymes for use herein include protease, amylase, lipase, cellulase, carbohydrase including mannanase and endoglucanase, and mixtures thereof. Enzymes can be used at their art-taught levels, for example at levels recommended by suppliers such as Novo and Genencor. Typical levels in the compositions are from about 0.0001% to about 5%. When enzymes are present, they can be used at very low levels, e.g., from about 0.001% or lower, in certain embodiments of the invention; or they can be used in heavier-duty laundry detergent formulations in accordance with the invention at higher levels, e.g., about 0.1% and higher. In accordance with a preference of some consumers for "non-biological" detergents, the present invention includes both enzyme-containing and enzyme-free embodiments.

Deposition Aid

As used herein, "deposition aid" refers to any cationic polymer or combination of cationic polymers that significantly enhance the deposition of the fabric care benefit agent onto the fabric during laundering. An effective deposition aid preferably has a strong binding capability with the water insoluble fabric care benefit agents via physical forces such as van der Waals forces or non-covalent chemical bonds such as hydrogen bonding and/or ionic bonding. It preferably has a very strong affinity to natural textile fibers, particularly cotton fibers.

Preferably, the deposition aid is a cationic or amphoteric polymer. The amphoteric polymers of the present invention will also have a net cationic charge, i.e.; the total cationic charges on these polymers will exceed the total anionic charge. The cationic charge density of the polymer ranges from about 0.05 milliequivalents/g to about 6 milliequivalents/g. The charge density is calculated by dividing the number of net charge per repeating unit by the molecular weight of the repeating unit. In one embodiment, the charge density varies from about 0.1 milliequivants/g to about 3 milliequivalents/g. The positive charges could be on the backbone of the polymers or the side chains of polymers.

Nonlimiting examples of deposition aids are cationic polysaccharides, chitosan and its derivatives and cationic synthetic polymers. More particularly preferred deposition aids are selected from the group consisting of cationic hydroxy ethyl cellulose, cationic starch, cationic guar derivatives and mixtures thereof.

Commercially available cellulose ethers of the Structural Formula I type include the JR 30M, JR 400, JR 125, LR 400 and LK 400 polymers, all of which are marketed by Amerchol Corporation, Edgewater N.J. and Celquat H200 and Celquat L-200 available from National Starch and Chemical Company or Bridgewater, N.J. Cationic starches are commercially available from National Starch and Chemical Company under the Trade Name Cato. Examples of cationic guar gums are Jaguar C13 and Jaguar Excel available from Rhodia, Inc of Cranburry N.J. Nonlimiting examples of preferred polymers according to the present invention include copolymers comprising a) a cationic monomer selected from a group consisting N,N-dialkylaminoalkyl methacrylate, N,N-dialkylaminoalkyl acrylate, N,N-dialkylaminoalkyl acrylamide, N,N-dialkylaminoalkylmethacrylamide, their quaternized deriavtives, vinylamine and its derivatives, allylamine and its derivatives, vinyl imidazole, quaternized vinyl imidazole and diallyl dialkyl ammonium chloride.

b) And a second monomer selected from a group consisting of acrylamide (AM), N,N-dialkyl acrylamide, methacrylamide, N,N-dialkylmethacrylamide, C1-C12 alkyl acrylate, C1-C12 hydroxyalkyl acrylate, C1-C12 hydroxyetheralkyl acrylate, C1-C12 alkyl methacrylate, C1-C12 hydroxyalkyl methacrylate, vinyl acetate, vinyl alcohol, vinyl formamide, vinyl acetamide, vinyl alkyl ether, vinyl butyrate and derivatives and mixtures thereof.

The most preferred polymers are poly(acrylamide-co-diallyldimethylammonium chloride), poly(acrylamide-methacrylamidopropyltrimethyl ammonium chloride), poly(acrylamide-co-N,N-dimethyl aminoethyl methacrylate), poly(acrylamide-co-N,N-dimethyl aminoethyl methacrylate), poly(hydroxyethylacrylate-co-dimethyl aminoethyl methacrylate), poly(hydroxpropylacrylate-co-dimethyl aminoethyl methacrylate), poly(hydroxpropylacrylate-co-methacrylamidopropyltrimethylammonium chloride).

Builder

The compositions of the present invention may optionally comprise a builder. Suitable builders are discussed below:

Suitable polycarboxylate builders include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxy-disuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Oxydisuccinates are also especially useful in such compositions and combinations.

Also suitable in the liquid compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the C5-C20 alkyl and alkenyl succinic acids and salts thereof. A particularly preferred compound of this type is do-decenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in EP-A-0 200 263, published Nov. 5, 1986.

Specific examples of nitrogen-containing, phosphor-free aminocarboxylates include ethylene diamine disuccinic acid and salts thereof (ethylene diamine disuccinates, EDDS), ethylene diamine tetraacetic acid and salts thereof (ethylene diamine tetraacetates, EDTA), and diethylene triamine penta acetic acid and salts thereof (diethylene triamine penta acetates, DTPA).

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Bleach System

Bleach system suitable for use herein contains one or more bleaching agents. Nonlimiting examples of suitable bleaching agents are selected from the group consisting of catalytic metal complexes, activated peroxygen sources, bleach activators, bleach boosters, photobleaches, bleaching enzymes, free radical initiators, and hyohalite bleaches.

Suitable activated peroxygen sources include, but are not limited to, preformed peracids, a hydrogen peroxide source in combination with a bleach activator, or a mixture thereof. Suitable preformed peracids include, but are not limited to, compounds selected from the group consisting of percarboxylic acids and salts, percarbonic acids and salts, perimidic acids and salts, peroxymonosulfuric acids and salts, and mixtures thereof. Suitable sources of hydrogen peroxide include, but are not limited to, compounds selected from the group consisting of perborate compounds, percarbonate compounds, perphosphate compounds and mixtures thereof. Suitable types and levels of activated peroxygen sources are found in U.S. Pat. Nos. 5,576,282, 6,306,812 and 6,326,348.

Perfume

Perfumes are preferably incorporated into the detergent compositions of the present invention. The perfume ingredients may be premixed to form a perfume accord prior to adding to the detergent compositions of the present invention. As used herein, the term "perfume" encompasses individual perfume ingredients as well as perfume accords. More preferably the compositions of the present invention comprise perfume microcapsules. Perfume microcapsules comprise perfume raw materials encapsulated within a capsule made of materials selected from the group consisting of urea and formaldehyde, melamine and formaldehyde, phenol and formaldehyde, gelatine, polyurethane, polyamides, cellulose ethers, cellulose esters, polymethacrylate and mixtures thereof. Encapsulation techniques can be found in "Microencapsulation": methods and industrial applications edited by Benita and Simon (marcel Dekker Inc 1996).

The level of perfume accord in the detergent composition is typically from about 0.0001% to about 2% or higher, e.g., to about 10%; preferably from about 0.0002% to about 0.8%, more preferably from about 0.003% to about 0.6%, most preferably from about 0.005% to about 0.5% by weight of the detergent composition.

The level of perfume ingredients in the perfume accord is typically from about 0.0001% (more preferably 0.01%) to about 99%, preferably from about 0.01% to about 50%, more preferably from about 0.2% to about 30%, even more preferably from about 1% to about 20%, most preferably from about 2% to about 10% by weight of the perfume accord. Exemplary perfume ingredients and perfume accords are disclosed in U.S. Pat. Nos. 5,445,747; 5,500,138; 5,531,910; 6,491,840; and U.S. Pat. No. 6,903,061.

Solvent System

The solvent system in the present compositions can be a solvent system containing water alone or mixtures of organic solvents with water. Preferred organic solvents include 1,2-propanediol, ethanol, glycerol, dipropylene glycol, methyl propane diol and mixtures thereof. Other lower alcohols, $C_1$-$C_4$ alkanolamines such as monoethanolamine and triethanolamine, can also be used. Solvent systems can be absent, for example from anhydrous solid embodiments of the invention, but more typically are present at levels in the range of from about 0.1% to about 98%, preferably at least about 10% to about 95%, more usually from about 25% to about 75%.

Fabric Substantive and Hueing Dye

Dyes are conventionally defined as being acid, basic, reactive, disperse, direct, vat, sulphur or solvent dyes, etc. For the purposes of the present invention, direct dyes, acid dyes and reactive dyes are preferred, direct dyes are most preferred. Direct dye is a group of water-soluble dye taken up directly by fibers from an aqueous solution containing an electrolyte, presumably due to selective adsorption. In the Color Index system, directive dye refers to various planar, highly conjugated molecular structures that contain one or more anionic sulfonate group. Acid dye is a group of water soluble anionic dyes that is applied from an acidic solution. Reactive dye is a group of dyes containing reactive groups capable of forming covalent linkages with certain portions of the molecules of natural or synthetic fibers. From the chemical structure point of view, suitable fabric substantive dyes useful herein may be an azo compound, stilbenes, oxazines and phthalocyanines.

Suitable fabric substantive dyes for use herein include those listed in the Color Index as Direct Violet dyes, Direct Blue dyes, Acid Violet dyes and Acid Blue dyes.

In one preferred embodiment, the fabric substantive dye is an azo direct violet 99, also known as DV99 dye having the following formula:

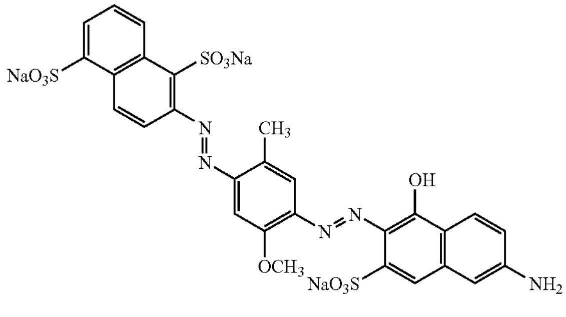

Hueing dyes may be present in the compositions of the present invention. Such dyes have been found to exhibit good tinting efficiency during a laundry wash cycle without exhibiting excessive undesirable build up during laundering.

The hueing dye is preferably included in the laundry detergent composition in an amount sufficient to provide a tinting effect to fabric washed in a solution containing the detergent. In one embodiment, the composition comprises, by weight, from about 0.0001% to about 0.05%, more specifically from about 0.001% to about 0.01%, of the hueing dye.

Exemplary dyes which exhibit the combination of hueing efficiency and wash removal value according to the invention include certain triarylmethane blue and violet basic dyes as set forth in Table 2, methine blue and violet basic dyes as set forth in Table 3, anthraquinone dyes as set forth in Table 4, anthraquinone dyes basic blue 35 and basic blue 80, azo dyes basic blue 16, basic blue 65, basic blue 66 basic blue 67, basic blue 71, basic blue 159, basic violet 19, basic violet 35, basic violet 38, basic violet 48, oxazine dyes basic blue 3, basic blue 75, basic blue 95, basic blue 122, basic blue 124, basic blue 141, Nile blue A and xanthene dye basic violet 10, and mixtures thereof.

Encapsulated Composition

The compositions of the present invention may be encapsulated within a water soluble film. The water-soluble film may be made from polyvinyl alcohol or other suitable variations, carboxy methyl cellulose, cellulose derivatives, starch, modified starch, sugars, PEG, waxes, or combinations thereof.

In another embodiment the water-soluble may include other adjuncts such as co-polymer of vinyl alcohol and a carboxylic acid. U.S. Pat. No. 7,022,656 B2 (Monosol) describes such film compositions and their advantages. One benefit of these copolymers is the improvement of the shelf-life of the pouched detergents thanks to the better compatibility with the detergents. Another advantage of such films is their better cold water (less than 10° C.) solubility. Where present the level of the co-polymer in the film material, is at least 60% by weight of the film. The polymer can have any weight average molecular weight, preferably from 1000 daltons to 1,000,000 daltons, more preferably from 10,000 daltons to 300,000 daltons, even more preferably from 15,000 daltons to 200,000 daltons, most preferably from 20,000 daltons to 150,000 daltons. Preferably, the co-polymer present in the film is from 60% to 98% hydrolysed, more preferably 80% to 95% hydrolysed, to improve the dissolution of the material. In a highly preferred execution, the co-polymer comprises from 0.1 mol % to 30 mol %, preferably from 1 mol % to 6 mol %, of said carboxylic acid.

The water-soluble film of the present invention may further comprise additional co-monomers. Suitable additional co-monomers include sulphonates and ethoxylates. An example of preferred sulphonic acid is 2-acrylamido-2-methyl-1-propane sulphonic acid (AMPS). A suitable water-soluble film for use in the context of the present invention is commercially available under tradename M8630™ from Mono-Sol of Indiana, US. The water-soluble film herein may also comprise ingredients other than the polymer or polymer material. For example, it may be beneficial to add plasticisers, for example glycerol, ethylene glycol, diethyleneglycol, propane diol, 2-methyl-1,3-propane diol, sorbitol and mixtures thereof, additional water, disintegrating aids, fillers, anti-foaming agents, emulsifying/dispersing agents, and/or antiblocking agents. It may be useful that the pouch or water-soluble film itself comprises a detergent additive to be delivered to the wash water, for example organic polymeric soil release agents, dispersants, dye transfer inhibitors. Optionally the surface of the film of the pouch may be dusted with fine powder to reduce the coefficient of friction. Sodium aluminosilicate, silica, talc and amylose are examples of suitable fine powders.

The encapsulated pouches of the present invention can be made using any convention known techniques. More preferably the pouches are made using horizontal form filling thermoforming techniques.

Other Adjuncts

Examples of other suitable cleaning adjunct materials include, but are not limited to, alkoxylated benzoic acids or salts thereof such as trimethoxy benzoic acid or a salt thereof (TMBA); enzyme stabilizing systems; chelants including aminocarboxylates, aminophosphonates, nitrogen-free phosphonates, and phosphorous- and carboxylate-free chelants; inorganic builders including inorganic builders such as zeolites and water-soluble organic builders such as polyacrylates, acrylate/maleate copolymers and the like scavenging agents including fixing agents for anionic dyes, complexing agents for anionic surfactants, and mixtures thereof; effervescent systems comprising hydrogen peroxide and catalase; optical brighteners or fluorescers; soil release polymers; dispersants; suds suppressors; dyes; colorants; filler salts such as sodium sulfate; hydrotropes such as toluenesulfonates, cumenesulfonates and naphthalenesulfonates; photoactivators; hydrolysable surfactants; preservatives; anti-oxidants; anti-shrinkage agents; anti-wrinkle agents; germicides; fungicides; color speckles; colored beads, spheres or extrudates; sunscreens; fluorinated compounds; clays; luminescent agents or chemiluminescent agents; anti-corrosion and/or appliance protectant agents; alkalinity sources or other pH adjusting agents; solubilizing agents; processing aids; pigments; free radical scavengers, and mixtures thereof. Suitable materials include those described in U.S. Pat. Nos. 5,705,464, 5,710,115, 5,698,504, 5,695,679, 5,686,014 and 5,646,101. Mixtures of adjuncts—Mixtures of the above components can be made in any proportion.

Composition Preparation

The compositions herein can preferably be prepared by first forming a pre-mix within which the rheology modifier is dispersed in a portion of the water eventually used to comprise the compositions. This pre-mix is formed in such a way that it comprises a structured liquid.

To this structured pre-mix can then be added, while the pre-mix is under agitation, the surfactant(s) and essential laundry adjunct materials, along with water and whatever optional detergent composition adjuncts are to be used. Any convenient order of addition of these materials, or for that matter, simultaneous addition of these composition components, to the pre-mix can be carried out. The resulting combination of structured premix with the balance of the composition components forms the aqueous liquid matrix to which the pearlescent agent will be added.

In a particularly preferred embodiment wherein a crystalline, hydroyxl-containing structurant is utilized, the following steps can be used to activate the structurant:

1) A premix is formed by combining the crystalline, hydroxyl-stabilizing agent, preferably in an amount of from about 0.1% to about 5% by weight of the premix, with water which comprises at least 20% by weight of the premix, and one or more of the surfactants to be used in the composition, and optionally, any salts which are to be included in the detergent composition.
2) The pre-mix formed in Step 1) is heated to above the melting point of the crystalline, hydroxyl-containing structurant.

3) The heated pre-mix formed in Step 2) is cooled, while agitating the mixture, to ambient temperature such that a thread-like structuring system is formed within this mixture.
4) The rest of the detergent composition components are separately mixed in any order along with the balance of the water, to thereby form a separate mix.
5) The structured pre-mix from Step 3 and the separate mix from Step 4 are then combined under agitation to form the structured aqueous liquid matrix into which the visibly distinct beads will be incorporated.

EXAMPLES

The following nonlimiting examples are illustrative of the present invention. Percentages are by weight unless otherwise specified.

Examples 1-5 illustrates the preparation of cold pearl premixes.

Example 1

To prepare a cold pearl premix, 900 grams SLS[1] is added to a jacketed vessel with an internal diameter of 120 mm and a total capacity of approximately 1200 ml. The vessel is equipped with dual four blade impellers at a length of 38 mm each and having a pitch of 45°. SLS is heated to 77° C. at which point 100 grams glycol ester-A[3] (EGDS:EGMS 75:25) is added. The pre-mix is held at 77° C. for approximately 2 hours at a mixing speed of 300 RPMs. The mixture is heated to 87° C. and held for 30 minutes while maintaining 300 RPM. It is then cooled at a rate of 4° C./min until the pre-mix reached 22° C. while maintaining 300 RPM. Once pre-mix has reached the desired temperature, mixing is stopped.

Example 2

To prepare a cold pearl premix, 900 grams ALS[2] and 100 grams glycol ester-A[3] (EGDS EGMS 75:25) are mixed according to the process described in Example 1.

Example 3

To prepare a cold pearl premix, 900 grams SLS[1] and 100 grams glycol ester-A[3] (EGDS:EGMS 60:40) are mixed according to a process similar to the process described in Example 1, except that the mixing speed is 200 RPM and the cooling rate is 2° C./min.

Example 4

To prepare a cold pearl premix, 900 grams SLS[1] and 100 grams glycol ester-B[4] are mixed according to the process described in Example 1.

Example 5

To prepare a cold pearl premix, 890 grams SLS[1] is added to a jacketed vessel with an internal diameter of 120 mm and a total capacity of approximately 1200 ml. The vessel is equipped with dual four blade impellers at a length of 38 mm each and having a pitch of 45°. SLS is heated to 77° C. at which point 100 grams glycol ester-C[5] (90:10) and 10 g C12-C14 fatty acid are added. The pre-mix is held at 77° C. for approximately 2 hours at a mixing speed of 250 RPMs. The pre-mix is heated to 87° C. and held for 30 minutes while maintaining 250 RPM. It is then cooled at a rate of 2° C./min until the pre-mix reached 22° C. while maintaining 250 RPM. Once pre-mix has reached the desired temperature, mixing is stopped 1: SLS=Sodium lauryl sulfate, available from Colonial Chemical Inc. South Pittsburg, Tenn. containing 29% active sodium lauryl sulfate.

2: ALS=Ammonium lauryl sulfate, available from The Stepan Company of Northfield, Ill. Chemical Inc. containing 30% active ammonium lauryl sulfate.

3: Glycol Ester-A a. Ethylene glycol disterarate (EGDS) available from Degussa, Hopewell Va., containing 98% ethylene glycol distearate and 2% ethylene glycol monostearate); and b. Ethylene glycol monostearate (EGMS), available from The Stepan Company, Northfield, Ill., containing 40% ethylene glycol distearate and 60% ethylene glycol monostearate). Components are mixed in the ratio of a:b=60:40 so as to achieve a final ratio of EGDS:EGMS of 75:25 for Glycol Ester—A.

4: Glycol Ester-B c. Ethylene glycol disterarate (EGDS) supplied by Degussa, Hopewell Va., containing 98% ethylene glycol distearate and 2% ethylene glycol monostearate).

5: Glycol Ester-C d. Ethylene glycol disterarate (EGDS) supplied by Degussa, Hopewell Va., containing 98% ethylene glycol distearate and 2% ethylene glycol monostearate); and e. Ethylene glycol monostearate (EGMS), supplied by The Stepan Company, Northfield, Ill. containing 40% ethylene glycol distearate and 60% ethylene glycol monostearate).

Components are mixed in a ratio of d:e=87:13 so as to achieve a final ratio of EGDS:EGMS of 90:10 for Glycol Ester—C.

An Example of a Liquid Detergent Composition Containing Cold Pearl

Cold pearl compositions of Examples 1-5 are mixed with liquid laundry detergents with stirring and without any externally applied heat. The resulting detergent compositions have an attractive pearlescent appearance as prepared.

Example 6

Detergent Compositions Containing Cold Pearl

| Ingredient | Wt % |
|---|---|
| C12-15alkyl polyethoxylate (1.8) sulfate | 18.0 |
| Ethanol | 2.5 |
| Diethylene glycol | 1.3 |
| Propanediol | 3.5 |
| C12-13Alkyl polyethoxylate (9) | 0.4 |
| C12-14 fatty acid | 2.5 |
| Sodium cumene sulfonate | 3.0 |
| Citric acid | 2.0 |
| Sodium hydroxide (to pH 8.0) | 1.5 |
| Protease (32 g/L) | 0.3 |
| Cold Pearl from example 1 to 5 | 2.0[#] |
| Soil suspending polymers | 1.1 |
| adjuncts* | <10 |
| Hydrogenated Castor Oil | 0.2 |
| Water | to 100% |

*adjuncts include perfume, enzymes, fabric softeners, suds suppressor, brightener, enzyme stabilizers & other optional ingredients.

[#]the concentration is based on the active (EGDS + EGMS) level in the cold pearl.

Example 7

A Compact Detergent Composition Containing Cold Pearls is Prepared According to the Procedure Above and the Compact Detergent Composition Exhibits Product Stability

| Ingredient | Wt % |
|---|---|
| C12-15alkyl polyethoxylate (1.8) sulfate | 28.0 |
| Ethanol | 3.9 |
| Diethylene glycol | 2.1 |
| Propanediol | 5.2 |
| C12-alkyl trimethyl ammonium chloride | 4.0 |
| C12-13Alkyl polyethoxylate (9) | 0.4 |
| C12-14 fatty acid | 4.5 |
| Sodium cumene sulfonate | 2.3 |
| Citric acid | 3.3 |
| Sodium hydroxide (to pH 8.0) | 1.5 |
| Protease (32 g/L) | 0.3 |
| Cold Pearl from Example 1 to 5 | 1.0[#] |
| Soil suspending polymers | 2.2 |
| adjuncts* | <10 |
| Hydrogenated Castor Oil | 0.2 |
| Water | to 100% |

adjuncts include perfume, enzymes, fabric softeners, suds suppressor, brightener, enzyme stabilizers & other optional ingredients.

[#]the concentration is based on the active (EGDS + EGMS) level in the cold pearl.

Examples 8 to 16 Reflect Concentrated Liquid Detergents According to the Present Invention

| Ingredient (assuming 100% activity) | 8 weight % | 9 weight % | 10 weight % | 11 Weight % | 12 weight % | 13 weight % |
|---|---|---|---|---|---|---|
| AES[1] | 21.0 | 12.6 | 21.0 | 12.6 | 21.0 | 5.7 |
| LAS[2] | — | 1.7 | — | 1.7 | — | 4.8 |
| Branched Alkyl sulfate | — | 4.1 | — | 4.1 | — | 1.3 |
| NI 23-9[3] | 0.4 | 0.5 | 0.4 | 0.5 | 0.4 | 0.2 |
| C12 trimethylammonium chloride[4] | 3.0 | — | 3.0 | — | 3.0 | — |
| Citric Acid | 2.5 | 2.4 | 2.5 | 2.4 | 2.5 | — |
| $C_{12-18}$ Fatty Acids | 3.4 | 1.3 | 3.4 | 1.3 | 3.4 | 0.3 |
| Protease B | 0.4 | 0.4 | 0.4 | 0.4 | 0.4 | 0.1 |
| Carezyme[5] | 0.1 | 0.1 | 0.1 | 0.1 | 0.1 | — |
| Tinopal AMS-X[6] | 0.1 | 0.1 | 0.1 | — | 0.1 | 0.3 |
| TinopalCBS-X[6] | — | — | — | | 0.1 | — |
| ethoxylated ($EO_{15}$) tetraethylene pentaimine[7] | 0.3 | 0.4 | 0.3 | 0.4 | 0.3 | 0.4 |
| PEI 600 $EO_{20}$[8] | 0.6 | 0.8 | 0.6 | 0.8 | 0.6 | 0.3 |
| Zwitterionic ethoxylated quaternized sulfated hexamethylene diamine[9] | 0.8 | — | 0.8 | — | 0.8 | — |
| PP-5495[10] | 3.4 | 3.0 | 3.4 | 3.0 | 3.4 | 2.7 |
| KF-889[11] | — | — | — | — | 3.4 | — |
| Acrylamide/MAPTAC[12] | 0.2 | 0.2 | 0.2 | 0.2 | — | 0.3 |
| Diethylene triamine penta acetate, MW = 393 | 0.2 | 0.3 | 0.2 | 0.2 | 0.2 | — |
| Mica/TiO2[13] | 0.2 | 0.1 | — | — | — | 0.1 |
| Ethyleneglycol distearate[14] | — | — | 1.0 | 1.0 | | — |
| Hydrogenated castor oil | 0.1 | 0.1 | 0.1 | 0.1 | 0.1 | 0.1 |
| water, perfumes, dyes, and other optional agents/components | to 100% balance | to 100% balance | to 100% balance | To 100% balance | to 100% balance | to 100% balance |

| Ingredient (assuming 100% activity) | 14 weight % | 15 weight % | 16 weight % |
|---|---|---|---|
| AES[1] | 21.0 | 12.6 | 21.0 |
| LAS[2] | — | 1.7 | — |
| Branched Alkyl sulfate | — | 4.1 | — |
| NI 23-9[3] | 0.4 | 0.5 | 0.4 |
| C12 trimethylammonium chloride | 3.0 | — | 3.0 |
| Citric Acid | 2.5 | 2.4 | 2.5 |
| $C_{12-18}$ Fatty Acids | 3.4 | 1.3 | 3.4 |
| Protease B | 0.4 | 0.4 | 0.4 |
| Carezyme[7] | 0.1 | 0.1 | 0.1 |
| Tinopal AMS-X[8] | 0.1 | 0.1 | 0.1 |
| TinopalCBS-X[8] | — | — | — |
| ethoxylated ($EO_{15}$) tetraethylene pentaimine[4] | 0.3 | 0.4 | 0.3 |
| PEI 600 $EO_{20}$[5] | 0.6 | 0.8 | 0.6 |
| Zwitterionic ethoxylated quaternized sulfated hexamethylene diamine[6] | 0.8 | — | 0.8 |
| PP-5495[9] | 3.4 | 3.0 | 3.4 |
| Mirapol 550[15] | 0.2 | 0.2 | 0.2 |
| Diethylene triamine penta | 0.2 | 0.3 | 0.2 |

-continued

| | | | |
|---|---|---|---|
| acetate, MW = 393 | | | |
| Mica/TiO2[11] | 0.2 | — | 0.1 |
| Ethyleneglycol distearate[12] | | 1.0 | — |
| Hydrogenated castor oil | 0.1 | 0.1 | 0.1 |
| water, perfumes, dyes, and other optional agents/components | to 100% balance | to 100% balance | to 100% balance |

[1]$C_{10}$-$C_{18}$ alkyl ethoxy sulfate
[2]$C_9$-$C_{15}$ linear alkyl benzene sulfonate
[3]$C_{12}$-$C_{13}$ ethoxylated ($EO_9$) alcohol
[4]Supplied by Akzo Chemicals, Chicago, IL
[5]Supplied by Novozymes, NC
[6]Supplied by Ciba Specialty Chemicals, high Point, NC
[7]as described in U.S. Pat. No. 4,597,898
[8]as described in U.S. Pat. No. 5,565,145
[9]available under the tradename LUTENSIT ® from BASF and such as those described in WO 01/05874
[10]supplied by Dow Corning Corporation, Midland, MI
[11]supplied by Shin-Etsu Silicones, Akron, OH
[12]supplied by Nalco Chemcials of Naperville, IL
[13]supplied by Ekhard America, Louisville, KY
[14]Supplied by Degussa Corporation, Hopewell, VA
[15]Supplied by Rhodia Chemie, France
[16]Supplied by Aldrich Chemicals, Greenbay, WI
[17]Supplied by Dow Chemicals, Edgewater, NJ
[18]Supplied by Shell Chemicals

Further Examples

| | Liquid detergent Example 17: | Liquid detergent Example 18: | Liquid Unidose Example 19* |
|---|---|---|---|
| C14-C15 alkyl poly ethoxylate (8) | 6.25 | 4.00 | |
| C12-C14 alkyl poly ethoxylate (7) | | | 16.7 |
| C12-C14 alkyl poly ethoxylate (3) sulfate Na salt | 10.60 | 6.78 | |
| Linear Alkylbenzene sulfonate acid | 0.79 | 1.19 | 22.8 |
| Citric Acid | 3.75 | 2.40 | |
| C12-C18 Fatty Acid | 7.02 | 4.48 | 18.0 |
| Enzymes | — | 1.0 | 1 |
| Boric Acid | 1.25 | 1.25 | |
| Trans-sulphated ethoxylated hexamethylene diamine quat | 1.11 | 0.71 | |
| Diethylene triamine penta methylene phosphonic acid | 0.17 | 0.11 | |
| Fluorescent brightener | — | 0.06 | 0.30 |
| Polyquaternium 10 - Cationic hydroxyl ethyl cellulose | 0.470 | — | |
| Hydrogenated Castor Oil | 0.300 | 0.300 | 0.20 |
| Mono Ethanol Amine | | | 6.8 |
| Ethanol | 2.50 | 1.00 | |
| 1,2 propanediol | 1.14 | 0.04 | 13.2 |
| Poly dimethyl siloxane | | | 2.2 |
| Potassium Sulphite | | | 0.2 |
| Glycerol | | | 7 |
| Sodium hydroxide | 4.60 | 3.01 | 1.0 |
| Silicone emulsion | 0.0030 | 0.0030 | |
| Blue Dye | 0.00084 | 0.00084 | ppm |
| Mica/$TiO_2$ - Prestige Silk Silver Star - Eckart | — | 0.1 | |
| BiOCl - Biron Silver CO - Merck | 0.18 | — | 0.2 |
| Perfume | 1.00 | 0.65 | 1.6 |
| Water | Up to 100 | Up to 100 | Up to 100 |

*Unitized Dose composition comprising liquid composition enveloped within a water-soluble film.

The following composition was prepared in lab scale batches as well as pilot plant scale in a continuous liquid process. The product was then packaged in water-soluble film pouches of 45 mL. The water-soluble film is from Monosol type M8630. The resulting unitized dose products were monitored over a period of 4 months at 35° C. for physical stability and appearance. The products exhibited good stability, meaning no visual splitting or settling of the pearlescent material from the composition.

Example 20 & 21

Liquid Laundry Detergents

| Ingredient | Example 20 Wt % | Example 21 Wt % |
|---|---|---|
| C12 Linear Alkylbenzene Sulfonate Na salt | 10 | 10 |
| C12-15 alkyl poly ethoxylate (2) sulfate Na salt | 10 | 10 |
| C12-14 alkyl polyethoxylate (9) | 10 | 10 |
| C12-18 Fatty acid Na salt | 5.5 | 5.5 |
| Citric acid | 3 | 3 |
| Dequest 2010[1] | 1 | 1 |
| 1,2 propanediol | 4 | 0 |
| Di propylene Glycol | 4 | 8 |
| Polycarboxylate (Carbopol Aqua 30) | 3 | 3 |
| Monoethanolamine | 3 | 3 |
| Mica Pearlescent agent[2] | 0.2 | — |
| Biron Silver CO[3] | — | 0.2 |
| Adjuncts[4] | <10 | <10 |
| Water | Up to 100 | Up to 100 |

[1]Dequest ® 2010: Hydroxyethylidene 1,1 diphosphonic acid Na salt (ex Solutia)
[2]Prestige Silk Silver Star from Eckart Pigments (Particle size range: 5-25 μm, average Particle Size 10 μm, D0.99 29.70 μm)
[3]Biron Silver CO from Merck, 70% dispersion of bismuth oxychloride in castor oil
[4]Adjuncts include perfume, enzymes, fabric softeners, suds suppressors, brightener, enzyme stabilizers & other optional ingredients.

What is claimed is:

1. A pearlescent liquid laundry treatment composition cleaning composition comprising in a liquid medium:

a rheology modifier providing high shear viscosity at $20s^{-1}$ and 21° C. of from about 1 to about 1500 cps and low shear viscosity at 0.05 $sec^{-1}$ at 21° C. of greater than 5000 cps;

an organic pearlescent agent suspended in the liquid medium and having a refractive index greater than 1.41, such that the refractive-index difference ($\Delta n$) of the liquid medium and the organic pearlescent agent is greater than 0.02, the organic pearlescent agent having the formula:

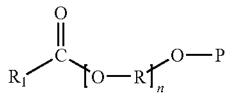

where $R_1$ is a linear or branched C12-C22 alkyl chain;

R is a linear or branched C2-C4 alkylene group;

P is selected from the group consisting of H, C1-C4 alkyl, and —$COR_2$, where $R_2$ is C4-C22 alkyl; and n is from 1 to 3;

from 5% to 30% by weight, based on the weight of the pearlescent liquid laundry treatment composition, of a C12-C22 fatty ester co-crystallizing agent;

from 1% to 5% by weight, based on the weight of the pearlescent liquid laundry treatment composition, of a C12-C22 fatty alcohol or fatty acid co-crystallizing agent, such that the weight ratio of the fatty ester co-crystallizing agent to the fatty alcohol or fatty acid co-crystallizing agent is from about 5:1 to about 20:1; and a laundry care benefit agent selected from the group consisting of polyolefin waxes, latexes, oily sugar derivatives, cationic polysaccharides, polyurethanes, and mixtures thereof.

2. The pearlescent liquid laundry treatment composition of claim 1, wherein the rheology modifier is selected from: non-polymeric crystalline hydroxy-containing fatty acids; polymeric gums; polycarboxylate polymers; non-gum polysaccharides; and mixtures thereof.

3. The pearlescent liquid laundry treatment composition of claim 1, wherein the rheology modifier is selected from: polymeric gums; non-polymeric crystalline hydroxy-containing fatty acids; fatty esters; fatty waxes; and mixtures thereof.

4. The pearlescent liquid laundry treatment composition of claim 1, wherein the rheology modifier is selected from: guar gum; gum Arabic; gum tragacenth; karaya gum; locust bean gum; pectin; dextran; gellan gum; rhamsan gum; welan gum; xanthan gum; carboxymethyl cellulose; methyl hydroxypropyl cellulose; hydroxy propyl cellulose; hydroxyethyl cellulose; propylene glycol alginate; hydroxypropyl guar; carrageenan gum; furcellaran; hydrogenated castor oil derivatives; 1,4-di O-benzyl-D-Threitol; and mixtures thereof.

5. The pearlescent liquid laundry treatment composition of claim 1, wherein the rheology modifier is selected from: pectine; alginate; arabinogalactan; carrageenan; gellan gum; xanthan gum; guar gum; hydrogenated castor oil; hydrogenated castor wax; and mixtures thereof.

6. The pearlescent liquid laundry treatment composition of claim 1, further comprising an inorganic pearlescent agent selected from the group consisting of mica; metal oxide coated mica; bismuth oxychloride coated mica; bismuth oxychloride; glass; metal oxide coated glass; and mixtures thereof.

7. The pearlescent liquid laundry treatment composition of claim 1, wherein the composition is packaged in a water-soluble film.

8. A method for treating a substrate in need of treatment, the method comprising contacting the substrate with a pearlescent liquid laundry treatment composition of claim 1, such that the substrate is treated.

9. The pearlescent liquid laundry treatment composition of claim 1, comprising from 0.1% to 0.5% by weight, based on the weight of the pearlescent liquid laundry treatment composition, of the rheology modifier.

10. The pearlescent liquid laundry treatment composition of claim 9, wherein the rheology modifier is hydrogenated castor oil.

11. The pearlescent liquid laundry treatment composition of claim 10, further comprising:

an ethylhexylhydroxystearate suspending agent; and an inorganic pearlescent agent selected from the group consisting of mica; metal oxide coated mica; bismuth oxychloride coated mica; bismuth oxychloride; glass; metal oxide coated glass; and mixtures thereof.

12. The pearlescent liquid laundry treatment composition of claim 1, wherein the organic pearlescent agent is selected from the group consisting of ethylene glycol monostearate, ethylene glycol distearate, polyethylene glycol monostearate, polyethylene glycol distearate, and mixtures thereof.

13. The pearlescent liquid laundry treatment composition of claim 1, wherein the organic pearlescent agent is a mixture of an ethylene glycol diester and an ethylene glycol monoester, such that the weight ratio of the ethylene glycol diester to the ethylene glycol monoester in the mixture is from about 1:2 to about 2:1.

14. The pearlescent liquid laundry treatment composition of claim 1, wherein the organic pearlescent agent is a mixture of ethylene glycol distearate and ethylene glycol monostearate, such that the weight ratio of the ethylene glycol distearate to the ethylene glycol monostearate in the mixture is from about 60:40 to about 50:50.

15. The pearlescent liquid laundry treatment composition of claim 1, wherein the rheology modifier is selected from the group consisting of hydrogenated castor-oil derivatives and 1,4-di-O-benzyl-D-threitol.

* * * * *